(12) United States Patent
Korpi

(10) Patent No.: US 8,563,879 B2
(45) Date of Patent: Oct. 22, 2013

(54) INERTIAL MICROBALANCE FILTER ASSEMBLY

(75) Inventor: David Michael Korpi, Pacific Grove, CA (US)

(73) Assignee: Sierra Instruments, Monterey, CA (US)

( * ) Notice: Subject to any disclaimer, the term of this patent is extended or adjusted under 35 U.S.C. 154(b) by 779 days.

(21) Appl. No.: 12/757,808

(22) Filed: Apr. 9, 2010

(65) Prior Publication Data

US 2010/0258357 A1    Oct. 14, 2010

Related U.S. Application Data

(60) Provisional application No. 61/168,557, filed on Apr. 10, 2009.

(51) Int. Cl.
*G01G 3/16* (2006.01)
*G01G 21/28* (2006.01)
*B29D 23/00* (2006.01)
*G01N 5/00* (2006.01)

(52) U.S. Cl.
USPC ..... 177/210 FP; 73/19.03; 73/580; 428/36.9; 138/108

(58) Field of Classification Search
USPC ............... 73/19.03, 580; 428/36.9; 138/108; 177/210 FP
See application file for complete search history.

(56) References Cited

U.S. PATENT DOCUMENTS

| | | | | |
|---|---|---|---|---|
| 4,391,338 A * | 7/1983 | Patashnick et al. | ..... | 177/210 FP |
| 4,938,389 A * | 7/1990 | Rossi et al. | ............. | 222/189.08 |
| 5,184,946 A * | 2/1993 | Sato | ............................ | 417/423.9 |
| 5,205,153 A * | 4/1993 | Hlavinka et al. | ............. | 73/19.03 |
| 5,252,369 A * | 10/1993 | Akao et al. | .................... | 428/36.9 |
| 5,419,373 A * | 5/1995 | May | ............................... | 138/108 |
| 5,669,578 A * | 9/1997 | Ma | ............................... | 242/613.5 |
| 5,845,859 A * | 12/1998 | Sato | ............................... | 242/613 |
| 5,967,455 A * | 10/1999 | Farber | ........................ | 242/614.1 |
| 6,003,807 A * | 12/1999 | Ripplinger | ................. | 242/614.1 |
| 6,444,927 B1* | 9/2002 | Korpi | ...................... | 177/210 FP |
| 6,475,269 B1* | 11/2002 | Turner | ............................ | 96/134 |
| 6,966,444 B2* | 11/2005 | Morgan | ......................... | 210/448 |
| 2006/0233991 A1* | 10/2006 | Humphrey et al. | ......... | 428/36.91 |
| 2009/0036971 A1* | 2/2009 | Humphrey et al. | ........... | 623/1.15 |

FOREIGN PATENT DOCUMENTS

| | | | |
|---|---|---|---|
| DE | 4122241 A1 | * | 1/1993 |
| DE | 19917558 | * | 11/2000 |
| DE | 102007006772 A1 | * | 8/2008 |
| EP | 1941920 A1 | * | 7/2008 |
| JP | 2007-097818 | * | 4/2007 |

* cited by examiner

*Primary Examiner* — Randy W Gibson

(74) *Attorney, Agent, or Firm* — LaRiviere, Grubman & Payne, LLP

(57) ABSTRACT

A low tare weight filter system is disclosed. The low weight makes the system especially advantageous for use in inertial microbalance instrumentation where small variations in mass must be accounted for to deliver accurate results. Moreover, the assembly is constructed to permit the filter collector to flex and stretch over a complimentary body incorporated in a filter support base and securely fasten to the same. Such use offers further advantages for instrument performance. It insures consistent apposition and long-term stability in the contact between the filter media and its reference surface.

5 Claims, 3 Drawing Sheets

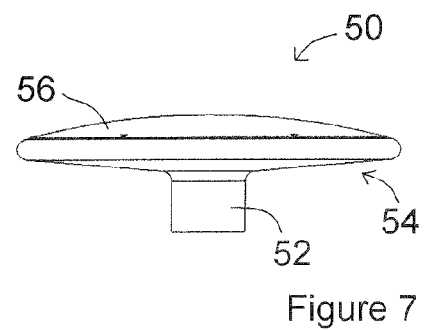
Figure 7
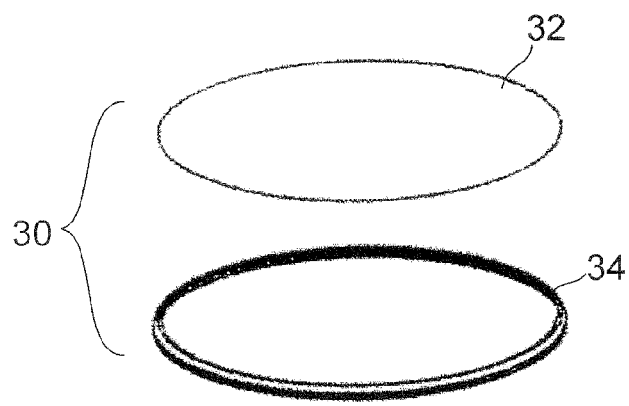
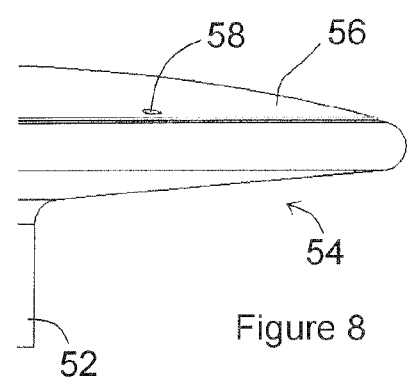
Figure 8
Figure 6
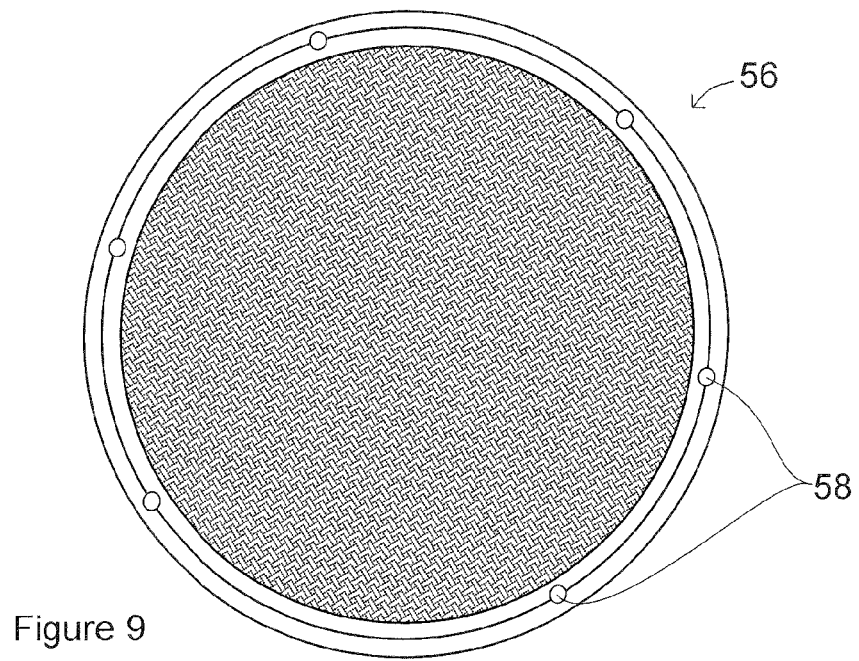
Figure 9

INERTIAL MICROBALANCE FILTER ASSEMBLY

PRIORITY CLAIM

This application claims priority to U.S. Provisional Patent Application No. 61/168,557, entitled Low Tare Weight Filter Design, filed on Apr. 10, 2009.

BACKGROUND

The present invention pertains to improvements in the design of particulate filter assemblies using a filter means and filter holding means that are used for real time particulate mass collection systems such as those described in the following patents: U.S. Pat. Nos. 7,285,736 and 6,444,927 and 6,205,842 and the many other variants utilizing a filter collection means integrated with a filter holding means to comprise a filter assembly for the purpose of collecting particulate in real time.

In these patents, a filter and filter holder is affixed to the end of a resonant structure, much like a tuning fork, and the mass of the filter is proportional to the frequency of oscillation. In these examples, the filter and filter holder are one and the same and the filter is not replaceable. In other words, the filter holding means are integrated into a single filter assembly where the filter collection means is securely fastened, to prevent leaks, to the filter holding means.

In practice, a clean filter and filter holder are attached to the end of the resonant structure and the resonant frequency of the filter and filter holder is recorded. As the filter loads up with particulate the mass of the filter and filter holder increases. Using the differences of resonant frequencies, one can infer the mass of the filter and filter holder in real time.

Problematic with existing filter and filter holder design is that they are relatively heavy. In know devices, weigh reduction has been pursued by reducing the mass of the filter holding means utilizing various geometrical designs that still maintain sufficient strength and rigidity to allow the filter holding means to survive in the operational environment. The present invention departs from this approach in accomplishing a goal of weight reduction to improve device performance. The present invention optimally offers other improvements to device performance as well.

SUMMARY

The present invention includes various features that may be practiced alone or in combination. In combination, they offer an especially advantageous arrangement and advancement measuring particulates with inertial microbalance devices.

One aspect of the invention comprises a filter collector and collector affixation assembly. Instead of associating the filter collector with a matrix of support structure, only the rim is secured. The subject assembly is constructed to permit the filter collector to flex and stretch from a flat starting condition. It is stretched over a convex (e.g., dome-shaped) body incorporated in a filter holder and securely fastened to the same. As elaborated upon below, this approach enables improved device sensitivity by eliminating device startup variability. Likewise, the elegant structure presents a very low tare weight to offer further improvement by separating the filter holding means from the filter collection means.

Another aspect of the invention comprises the holder to which the filter collector and collector affixation assembly is attached. It comprises each of an arch structure and a cup to back the filter collector. Preferably, the arch structure comprises a plurality of complex rib members. They may be "complex" in the sense that they may employ aircraft wing rib geometries or other truss patterns, taking the advantages so-offered (e.g., stability, stiffness and/or weight reduction) into an altogether different field of endeavor.

The present invention further comprises methods of manufacture. These methods may include not only those associated with creating the constituent components (e.g., as detailed below) but also their assembly to prepare a new (or refreshed) inertial microbalance for use.

BRIEF DESCRIPTION OF THE FIGURES

The figures provided herein are not necessarily drawn to scale, with some components and features are exaggerated for clarity. Of these:

FIG. 6 is an assembly view of the filter collector and collector affixation assembly;

FIG. 7 is a side view of the filter holder assembly;

FIG. 8 shows a close-up view of FIG. 7;

FIG. 9 is a top view of the filter support screen;

Variations of the invention from the embodiments pictured are contemplated. Accordingly, depiction of aspects and elements of the invention in the figures is not intended to limit the scope of the invention.

DETAILED DESCRIPTION

Exemplary embodiments of the invention are described below. Reference is made to the examples in a non-limiting sense. They are provided to illustrate more broadly applicable aspects of the present invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. All such modifications are intended to be within the scope of the claims made herein.

The drawings illustrate an exemplary embodiment of a 37 mm diameter filter collection means using an expanded PTFE (ePTFE) TELFON filter media secured to a chemically compatible support ring and utilizing an electroformed curved filter support screen. Other embodiments may employ another filter media, such as glass fiber or paper type filters (e.g., Whatman 41 Paper, Pallflex TX-40 paper, etc.) as well as filter support screens made utilizing other manufacturing methodologies such as chemically etching and sintered assemblies.

More generally, with separate filter holding and filter collection means as provided in the present invention, it is possible for the filter collection means to approach one tenth the mass of the entire filter assembly of known devices. The advantage of the reduction in tare weight is that the filter holding means can be optionally integrated into the resonant structure so that the change in resonant frequency will be fully reflective in the change in the mass of the filter collection means, and the particulate alone. Additionally, wet chemistry can be performed on the filter collection means without having to dissolve the filter holding means.

Figure 1:
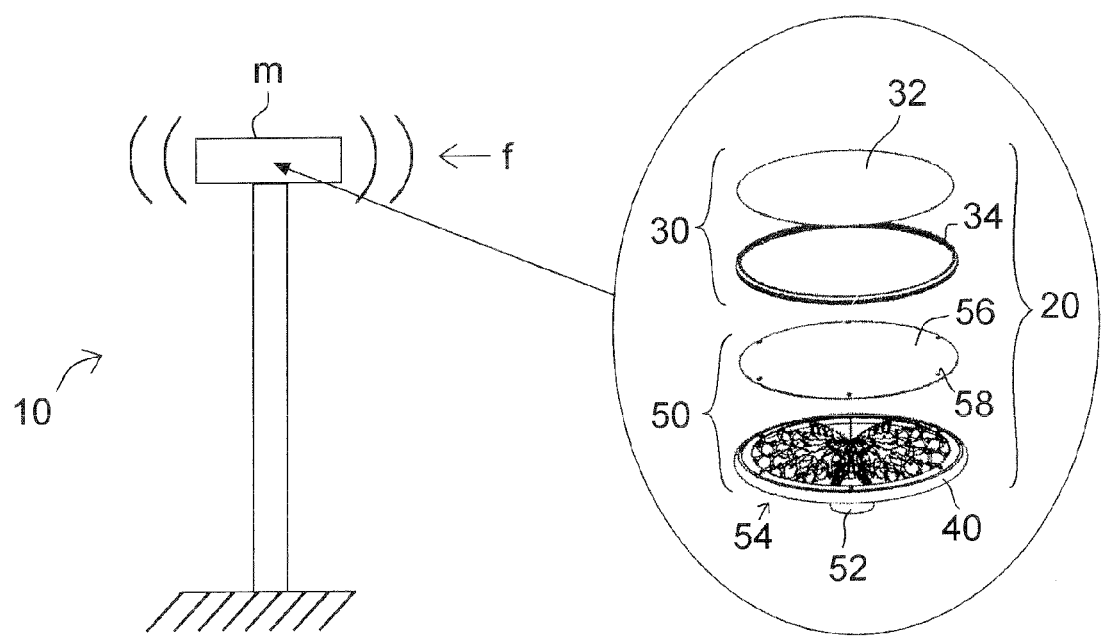
FIG. 1 pictures a resonant structure incorporating a filter means according to the present invention.

Turning to FIG. 1A, it shows a resonant structure 10 with a filter assembly, m, resonating at frequency, f, by virtue of the physics explained in the above mentioned patents. In this instance the mass, m, incorporates the filter assembly 20 of the present invention.

Figure 2:
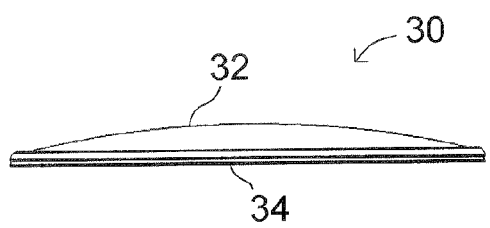
FIG. 2 is a side view of a filter collector and collector affixation assembly in its stretched configuration.

FIG. 2 shows a filter collection means (filter collector and collector affixation assembly) 30 including an ePTFE filter media (filter collector) 32 and a support ring (collector affixation ring) 34. The assembly 30 is shown in a stretched configuration over a slightly curved filter holding means (not shown).

The filter collection means is advantageously made of ePTFE material. The material may have a nominal thickness of about 50 microns. Such material may be bonded to a backing for support (e.g., TX-40 material by Pallflex Corporation). Such backing is typically a non woven material (e.g., glass fiber, quartz fiber, or borosilicate glass fibers) that may be between about 100 to about 500 microns thick.

Figure 3:
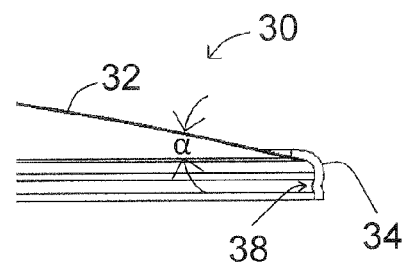
FIG. 3 is a cutaway view of the assembly shown in FIG. 2.

FIG. 3 shows a cutaway of FIG. 2 showing the filter collector 32 attachment to the filter support ring 34. Note that the filter collector media is attached on the interior of the filter support ring so that the filter is in intimate contact with the filter holding means when the system is assembled (see below). As such, the ring 34 and filter collector 32 can either flex to take-on a tangent take-off angle α around the rim of the support structure dome, or be formed to present a matching profile in its relaxed/original configuration.

The support ring material is advantageously selected to allow "welding" the ePTFE/TEFON filter media and support ring together. One means of doing so is to construct the support ring from FEP material. It has a lower melting the filter media and can wick into the interstices of the ePTFE matrix when heated. Polyolefin may alternatively be used. Ultrasonic bonding methods or resistance heater methods may be employed for the bonding operation. So-affixed, the filtration media is securely associated with the support ring without the generation of problematic artifacts.

Additionally, the support ring is designed so that it can slide firmly over the filter holding means (i.e., support base 50) and remain in place under vibrational loading. It is able to flex and fasten into place to make the attachment. Advantageously, it fastens with a snap-fit type interface with rim 38 fitting into a complementary groove 40 in the attachment body portion 52 of support base 50. Naturally, the male and female interface portions can be swapped. Moreover, another type of detent interface (e.g., a plurality of bumps and divots, etc.) can be used.

Figure 4:
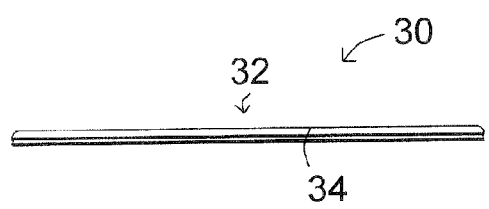
FIG. 4 is a side view of the filter collector and collector affixation assembly prior to it being installed on a filter holding assembly.

In any case, FIG. 4 shows filter assembly 30 in an as-built configuration prior to it being installed on the filter holding base/means. Comparison of FIGS. 2 and 4 illustrates the tuned construction of the system where the filter 32 and, optionally, support rim 34 will flex to intimately contact their respective support structures.

Figure 5:
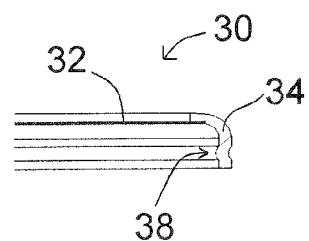
FIG. 5 is a cutaway view of the assembly shown in FIG. 4.

FIG. 5 shows a cutaway of FIG. 4 illustrating the TEFLON filter and support ring that comprise the filter collection means before the filter collection means is attached to the filter holding means. Note the TEFLON filter is attached on the interior of the support ring so that the TEFLON will be in intimate contact with the filter holding means after it is installed.

FIG. 6 shows the filter collector 32 and the filter support ring 34 before assembly. As configured per above and assembled, these form one independent aspect of the invention.

FIG. 7 shows filter holding/support base 50. It includes an interface region 52 for inertial microbalance attachment and a cupped air/vacuum communicating region 54 over which a filter support screen 56 is set. FIG. 8 shows a close up of FIG. 7. Note the filter support screen locating pins 58 that provide additional strength of the assembly. More important is the domed shape of the support screen. This shapes forces contact of the filter collection 32 at a stable position when the system is prepared for use. The dome shape also provides strength and rigidity to the screen itself. As such, it is able to stabily support the filter collector to provide an excellent reference surface, alone, while still being quite light in weight.

FIG. 9 shows support screen 56 as an electroformed or chemically etched piece. It can also be fabricated out of sintered material that provides for a similar porosity as illustrated.

Figure 10:
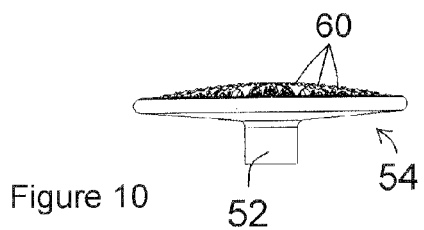
FIG. 10 is a side view of a filter holding base.

Underlying the region of the screen is a curved low mass support structure in the form of a plurality of support ribs 60 as shown if FIG. 10. The purpose of the support structure is not to buttress the screen, but rather to make the resonant frequency of the filter holder high so that it does not resonate or flex in an unwanted fashion.

Figure 11:
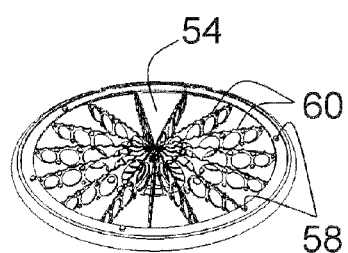
FIG. 11 is a perspective view of the filter holding base.
Figure 14:
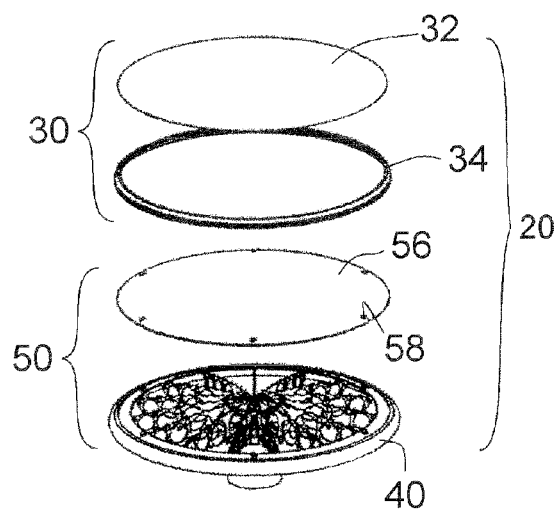
FIG. 14 is an assembly drawing of the subject filter means.
Figure 12:
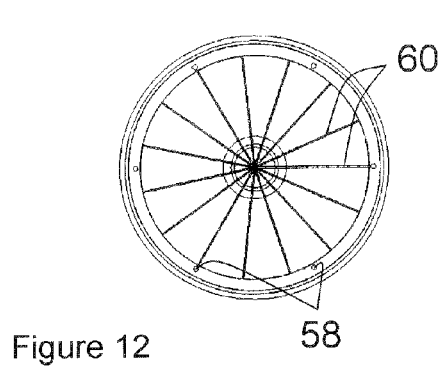
FIGS. 12 and 13 are top and bottom view of the filter holding base, respectively.
Figure 13:
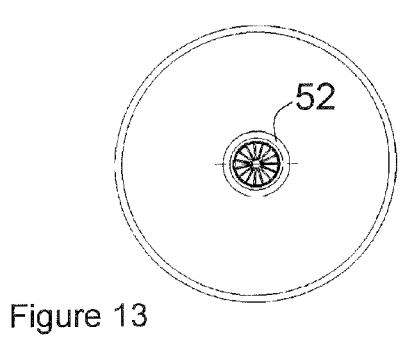

An advantageous construction for the support ribs is evident in FIG. 11. Note the similarity of low mass support structure to the structure of internal ribs in an airplane wing. Such an assembly is produced at reasonably cost (even as a monolithic body) and able to withstand the vibrations necessary utilizing high resolution SLA, SLS or 3D printing technology. FIG. 12 shows a top view of FIG. 10 with the low mass support structures providing additional detail as to their optional radial orientation/configuration. FIG. 13 shows a bottom view of this portion of the filter support base 50. It is open to allow air/vacuum transmission from the communicating region 54 of the overall filter support base 50. Finally, FIG. 14 shows an exploded drawing of the complete assembly.

Figure 15:
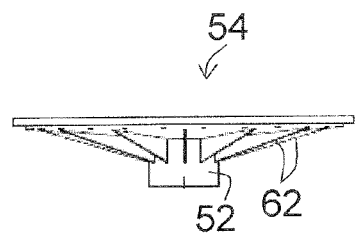
FIG. 15 is a side view of an alternative base.

The communicating region may comprise a circular cup. Such a form accommodates a support ribs as shown. However other shapes may be employed. An elliptical shape is one example. In which case, another rib support arrangement may be desirable. Note also, the base may employ an external rib/buttress structure in the support base as illustrated in FIG. 15. In which case, the communicating region may be totally flat, relying on the gap formed between its surface and the domed support screen to allow air/vacuum to pass into and through the support base.

Figure 16:
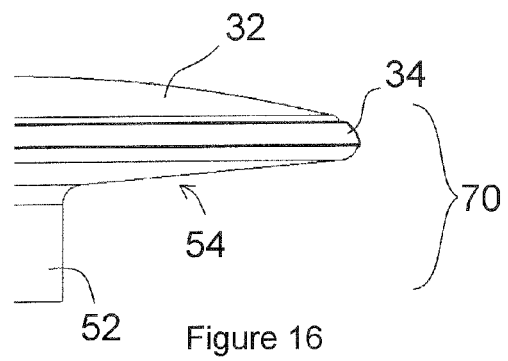
FIG. 16 is a side view of the completed filter assembly.

In any case, a complete inertial microbalance filter assembly 70 is shown in FIG. 16. As detailed, the filter collector 32 is stretched into a slight curvature so that the matrix from which it is produced is held tightly and firmly over the filter holding means (in this case the screen of the support base). Having this slight curvature allows for the filter collection means and filter holding means to be in intimate contact and to operate as an unmovable assembly.

In comparison, a filter collection means backed by a planar support surface bulges up from its flat support surface at least until a vacuum is established. In a resonant structure assembly this movement appears to be a decrease in mass and throws off the zero reading to a negative number. Actually, as the filter loads the filter media moves closer to the support means. Such movement toward the axis of device resonance causes an apparent decrease in the collected mass when in fact all that happened is the filter finally "seated" itself. The result is a negative indication of mass, when the opposite should be registered. Still further, the flat plane of the support screen will often bow inwardly as the filter becomes increasingly loaded with particulate. Not understanding these dynamics, manufacturers will frequently blame incorrect mass measurement trending on moisture evaporating. The correct explanation is that the filter becomes finally seated.

The present invention offers clear improvement in the basic design of filter assembly philosophy, thereby avoiding such problems. On one hand, the stretch of the filter over the screen provides a positive initial starting condition. And then, and the filter becomes loaded the dome shape of the filter offers the strength to provide a stable reference plane.

All said, it is contemplated that any optional feature of the inventive variations described may be set forth and claimed independently, or in combination with any one or more of the features described herein. Reference to a singular item, includes the possibility that there is a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of the claim language. All references cited are incorporated by reference in their entirety. Although the foregoing invention has been described in detail for purposes of clarity of understanding, it is contemplated that certain modifications may be practiced within the scope of the appended claims.

The invention claimed is:

1. A support base for an inertial microbalance instrument filter comprising:
   an attachment body, including a communicating region cupped in shape;
   an interface region for an inertial microbalance resonator;
   a plurality of support ribs; and
   a domed screen positioned over the communicating region, the ribs being positioned within the cupped region adjacent to the screen.

2. The base of claim 1, wherein the ribs are positioned external to the communicating region opposite the screen.

3. The base of claim 1, wherein the ribs are trussed.

4. A method of inertial microbalance instrument preparation, the method comprising the steps of:
   obtaining a filter collector and filter affixation assembly comprising an ePTFE disk and support ring including a radial detent for receipt upon a base, the ring and the disk in apposition around a periphery of the base;
   thermally bonding the disk and ring together;
   fitting the assembly onto a filter base included in the microbalance instrument to engage the ring detent; and
   stretching the ePTFE disk over a porous domed support surface in the base.

5. The method of claim 4, wherein the ring is made of a material selected from Polyolefin or FEP.

* * * * *